(12) United States Patent
Milliot et al.

(10) Patent No.: US 9,804,100 B2
(45) Date of Patent: Oct. 31, 2017

(54) DEVICE FOR SPRAYING A DYE PENETRATION INSPECTION LIQUID INTO A WORKPIECE

(71) Applicant: SNECMA, Paris (FR)

(72) Inventors: Josiane Milliot, Plaisir (FR); Yves Chucherko, Paris (FR); Jean-Michel Philippe, Sartrouville (FR)

(73) Assignee: SNECMA, Paris (FR)

( * ) Notice: Subject to any disclaimer, the term of this patent is extended or adjusted under 35 U.S.C. 154(b) by 117 days.

(21) Appl. No.: 14/412,774

(22) PCT Filed: Jun. 28, 2013

(86) PCT No.: PCT/FR2013/051530
§ 371 (c)(1),
(2) Date: Jan. 5, 2015

(87) PCT Pub. No.: WO2014/009629
PCT Pub. Date: Jan. 16, 2014

(65) Prior Publication Data
US 2015/0146198 A1 May 28, 2015

(30) Foreign Application Priority Data
Jul. 12, 2012 (FR) ..................................... 12 56745

(51) Int. Cl.
*B05B 13/02* (2006.01)
*B05B 15/08* (2006.01)
(Continued)

(52) U.S. Cl.
CPC ............. *G01N 21/91* (2013.01); *B05B 1/202* (2013.01); *B05B 9/007* (2013.01);
(Continued)

(58) Field of Classification Search
None
See application file for complete search history.

(56) References Cited

U.S. PATENT DOCUMENTS 3,620,234 A * 11/1971 Everroad ........... B01D 46/0071
134/102.1
4,661,379 A    4/1987 Frei et al.
(Continued)

FOREIGN PATENT DOCUMENTS

DE    92 06 996    10/1992
EP    0 093 083    11/1983
(Continued)

OTHER PUBLICATIONS

International Search Report dated Sep. 10, 2013 in PCT/FR13/051530 Filed Jun. 28, 2013.

*Primary Examiner* — Binu Thomas
(74) *Attorney, Agent, or Firm* — Oblon, McClelland, Maier & Neustadt, L.L.P.

(57) ABSTRACT

A device for spraying a liquid for use in dye penetration inspection into an inner cavity of a workpiece for making a turbine engine part, the device including a workpiece support, a manifold for spraying the inspection liquid into the inner cavity, a manifold for sucking up and discharging the sprayed inspection liquid, and a mechanism for tilting at least a portion of the support from a substantially horizontal position to an inclined position in which the workpiece is inclined so that the inspection liquid sprayed into the cavity flows under gravity to a zone from which it is sucked up.

16 Claims, 5 Drawing Sheets

(51) Int. Cl.

| | | |
|---|---|---|
| *B05C 7/02* | (2006.01) | |
| *B05C 11/10* | (2006.01) | |
| *B05C 13/00* | (2006.01) | |
| *G01N 21/91* | (2006.01) | |
| *B05B 13/06* | (2006.01) | |
| *B05B 1/20* | (2006.01) | |
| *B05B 9/00* | (2006.01) | |
| *B05B 15/04* | (2006.01) | |
| *B05C 7/04* | (2006.01) | |
| *B62B 3/08* | (2006.01) | |
| *F01D 21/00* | (2006.01) | |
| *G01M 15/14* | (2006.01) | |
| *B05B 15/00* | (2006.01) | |

(52) U.S. Cl.
CPC ...... *B05B 13/0221* (2013.01); *B05B 13/0627* (2013.01); *B05B 13/0645* (2013.01); *B05B 13/0672* (2013.01); *B05B 15/0406* (2013.01); *B05C 7/02* (2013.01); *B05C 7/04* (2013.01); *B05C 11/10* (2013.01); *B62B 3/08* (2013.01); *F01D 21/003* (2013.01); *G01M 15/14* (2013.01); *B05B 15/003* (2013.01); *B62B 2203/07* (2013.01); *F05D 2260/80* (2013.01); *G01N 2201/02* (2013.01)

(56) References Cited

U.S. PATENT DOCUMENTS

| | | | | |
|---|---|---|---|---|
| 4,965,099 | A * | 10/1990 | Bornhorst | B05D 7/227 118/408 |
| 8,118,948 | B1* | 2/2012 | Szabo | B08B 3/026 134/111 |
| 2013/0263898 | A1* | 10/2013 | Takei | B08B 3/042 134/157 |
| 2014/0193573 | A1* | 7/2014 | Kondoh | C23C 18/40 427/58 |

FOREIGN PATENT DOCUMENTS

| | | | |
|---|---|---|---|
| JP | 56 30634 | 3/1981 | |
| JP | 9 229875 | 9/1997 | |
| JP | WO 2012060047 A1 * | 10/2012 | |
| WO | WO 2013/039109 A1 * | 3/2013 | ............ C23C 18/40 |

* cited by examiner

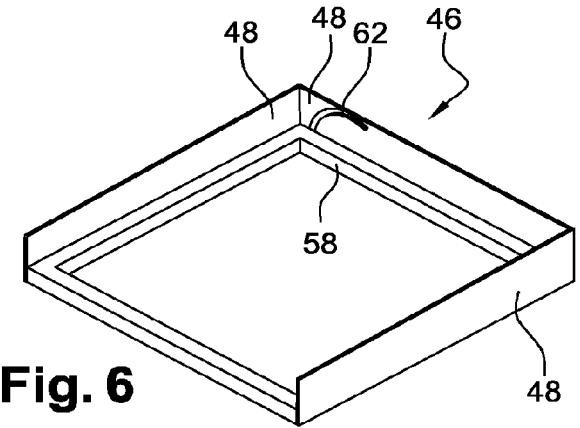
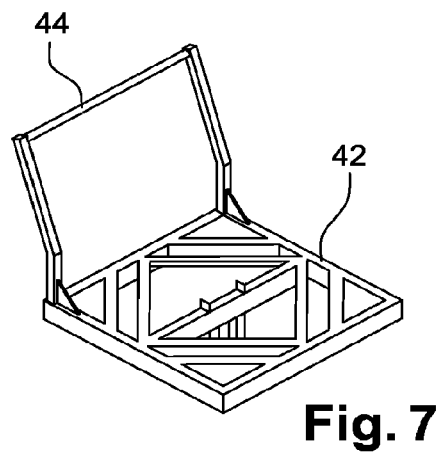
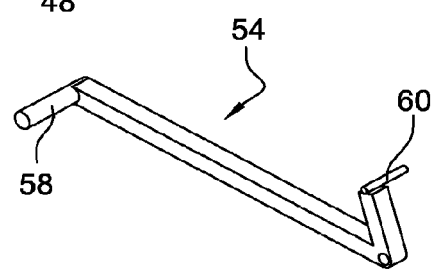

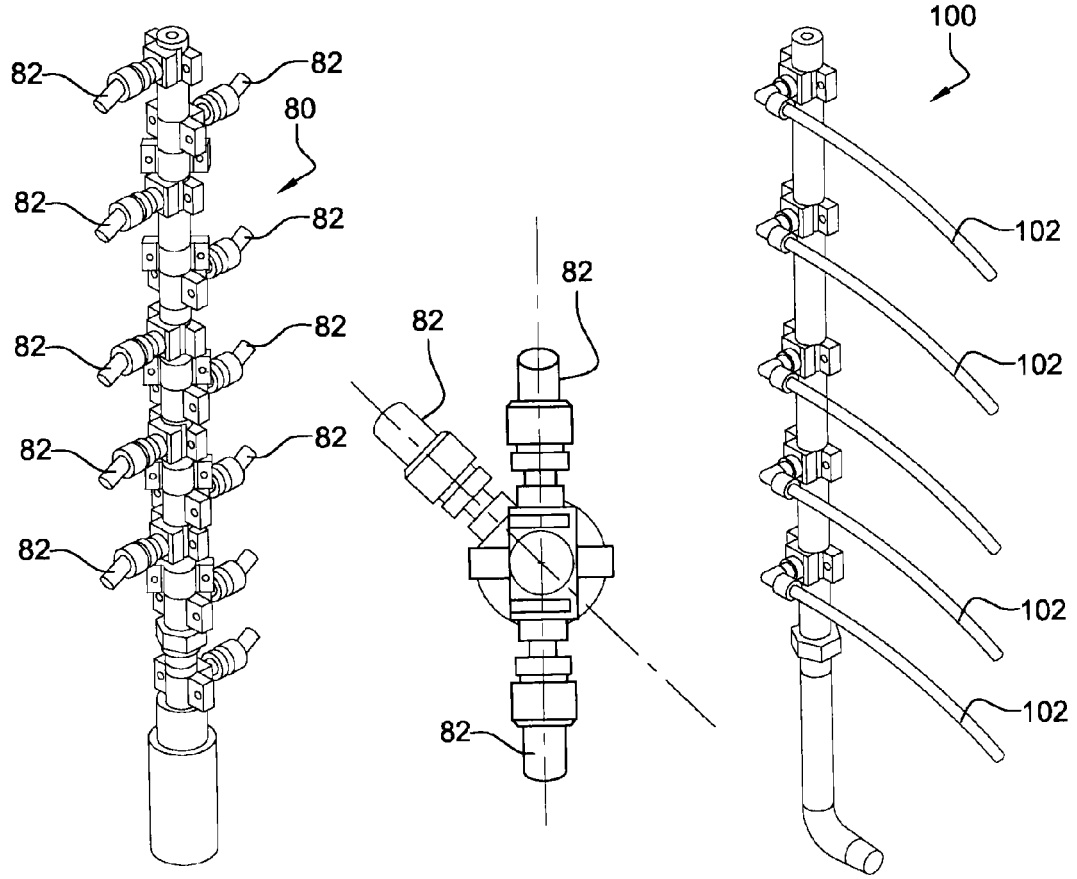
Fig. 9   Fig. 10   Fig. 11
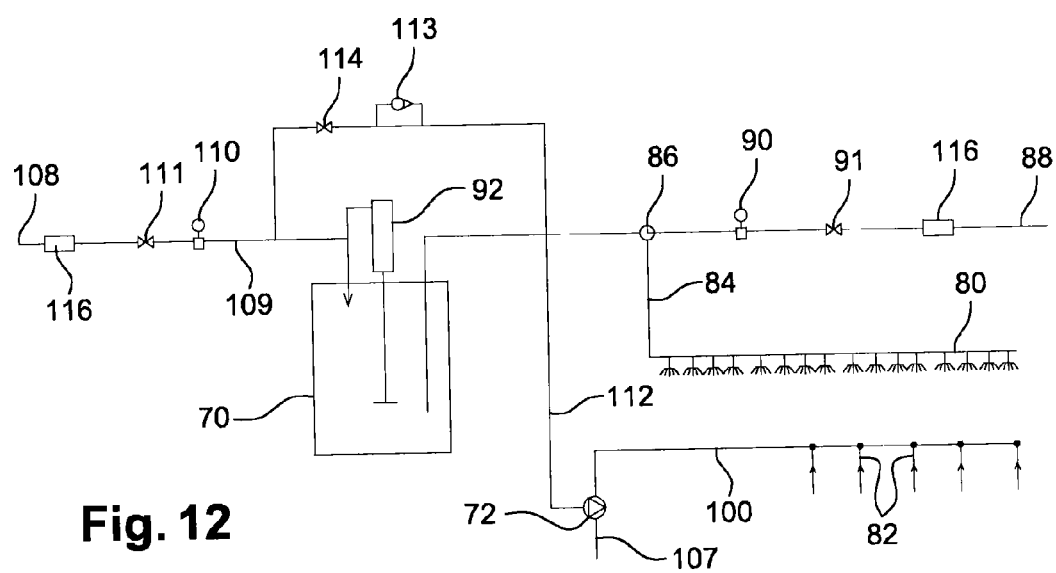
Fig. 12

DEVICE FOR SPRAYING A DYE PENETRATION INSPECTION LIQUID INTO A WORKPIECE

BACKGROUND OF THE INVENTION

Field of the Invention

The present invention relates to a device for spraying a liquid for use in dye penetration inspection onto a workpiece, in particular a turbine engine part.

Description of the Related Art

Documents EP-B1-1 494 060 and PCT/FR2012/050411 describe devices for searching for and detecting defects in a workpiece by dye penetration inspection and endoscopy.

Dye penetration is a non-destructive technique for inspecting the surface state of a part. The technique is based on the physical phenomenon of capillarity. The workpiece for inspection is covered in a highly wetting liquid referred to as a "penetrant" that penetrates into any defects of the workpiece and that is subsequently removed from the surface by washing the workpiece using at least one emulsifier and water. The workpiece is stoved in order to eliminate the water and then a developer is applied to the workpiece so that the penetrant held captive in the defects becomes visible when the workpiece is examined under ultraviolet light.

In the prior art, the stage of washing the workpiece is performed by immersing the workpiece in vessels containing emulsifier and water, respectively. However, when the workpiece for inspection is of large dimensions, such as for example a turbine engine drum, the vessels have dimensions that are very large. In addition, the weight and the size of the workpiece make that stage relatively complex and lengthy, particularly since the effectiveness of dye penetration inspection depends on well-controlled washing time.

A turbine engine drum comprises a plurality of rotor disks that are connected together and that define inner annular cavities between one another with walls that need to be inspected by dye penetration and that must therefore be washed with emulsifier and water. Unfortunately, those cavities are difficult to access. Totally immersing the workpiece in vessels of emulsifier and water serves to obviate that problem but takes much too much time and leads to relatively large amounts of emulsifier and water being consumed in order to fill the vessels.

There therefore exists a real need for a technology that is capable of processing a workpiece with a liquid for use in dye penetration inspection, such as in particular a turbine engine part of large size being processed with emulsifier and water, and enabling this to be done in a relatively short length of time, e.g. of the order of two minutes, and in a manner that is repeatable and reliable.

BRIEF SUMMARY OF THE INVENTION

The present invention satisfies this need and provides a solution to the problems of the prior art that is simple, effective, and inexpensive.

To this end, the invention provides a device for spraying at least one liquid, in particular for use in dye penetration inspection, into at least one inner cavity of a workpiece, in particular a turbine engine part, the device comprising:

- support means for supporting the workpiece;
- at least one liquid delivery manifold that is connected to liquid feed means and to spray means for spraying the liquid, the manifold being for receiving at least in part inside the workpiece when the workpiece is in position mounted on the support means so as to enable the liquid to be sprayed into the or each inner cavity of the workpiece;
- at least one recovery manifold for recovering the sprayed liquid, which manifold is for receiving at least in part inside the workpiece when the workpiece is in position mounted on the support means, and is connected to suction means for sucking up the liquid sprayed into the or each inner cavity of the workpiece, and to discharge means for discharging the sucked-up liquid; and
- tilting means for tilting at least a portion of the support means from a substantially horizontal position to an inclined position in which the workpiece is inclined so that the sprayed liquid in the or each cavity flows under gravity to at least one zone from which it is sucked up by the suction means.

In the device of the invention, the or each inspection liquid is sprayed into the or each cavity of the workpiece and is then sucked out from the or each cavity in order to be discharged by using manifolds that extend at least in part inside the workpiece, thus making it possible to avoid immersing the workpiece in the inspection liquid(s). The inspection liquid may be a penetrant, an emulsifier, a developer, a cleaning agent, etc. The delivery and recovery manifolds may also be used respectively for washing or rinsing the workpiece with water, and for recovering that water.

The invention may be applied to inspection of any workpiece having an inner cavity, and in particular a workpiece for constituting any rotary part or part constituting a body of revolution for a turbine engine.

The manifolds may extend in parallel and at a small distance apart from each other. Specifically when the workpiece for processing is a turbine engine drum, the manifolds may pass longitudinally through the drum and extend substantially parallel to the longitudinal axis or axis of revolution of the drum. Each cavity in the drum can receive the inspection liquid sprayed by two, three, or more independent spray means such as nozzles. The manifolds may be substantially rectilinear.

The suction manifold may carry flexible suction tubes that are spaced apart from one another, each having a free end that is to be received in an inner cavity of the workpiece.

The workpiece is for placing or mounting on the support means, which include at least one portion that is movable from a horizontal position to an inclined position. This movement enables the workpiece to be tilted into an inclined position that enables the sprayed inspection liquid to flow under gravity into one or more zones from which it is to be sucked up by the suction means.

In the above-specified example where the workpiece for processing is a drum, each cavity in the drum may include a zone into which the inspection liquid that has been sprayed into the cavity flows under gravity, and the recovery manifold may be connected to mutually independent suction means, each for the purpose of sucking up the inspection liquid that has accumulated in that zone of a respective cavity.

The delivery manifold may carry at least two series of spray nozzles, the nozzles in each series being spaced apart from one another and being situated in a plane that is substantially vertical and that is angularly offset from the plane of the or each other series of nozzles. Advantageously, the nozzles are of the steerable type.

The support means preferably comprise centering and guide means for guiding the workpiece in rotation about an axis that is preferably an axis of revolution of the workpiece.

Preferably, the workpiece is mounted on the support means in such a manner that its axis of revolution is substantially vertical.

The above-mentioned centering and guide means may comprise a first series of rollers, each free to rotate about an axis that is substantially perpendicular to the axis of rotation of the workpiece, and a second series of rollers, each free to rotate about an axis substantially parallel to the axis of rotation of the workpiece.

The support means may comprise a tray of substantially rectangular shape that is mounted on a frame and that is connected to the frame by pivot means enabling the tray to be pivoted relative to the frame about a substantially horizontal axis extending parallel to one of the sides of the tray.

The frame may have a substantially vertical peripheral rim extending around at least a fraction of the tray.

The tilting means may comprise a substantially L-shaped lever comprising a first substantially rectilinear portion connected to a second substantially rectilinear portion, the first portion carrying handle means, the junction zone between the first and second portions being hinged to the frame about a substantially horizontal axis, and the second portion carrying a finger that is engaged in and movable along a slot of curved shape in the peripheral rim of the frame and that co-operates with the tray to cause it to pivot when the finger moves along the slot.

The support means may be fitted with castors to enable the device to be moved.

The support means may include a support plate for supporting at least one tank of inspection liquid, such as an emulsifier, which tank is connected to the delivery manifold, and a pump connected to the recovery manifold.

The delivery manifold may be connected by a three-port valve to the tank for inspection liquid and to water feed means such as a water supply network. Under such circumstances, the delivery manifold serves to feed the spray means both with inspection liquid and with water.

The present invention also provides a method of spraying at least one liquid, in particular for use in dye penetration inspection, into at least one inner cavity of a workpiece, in particular a turbine engine part, by using a device as described above, the method being characterized in that it comprises the steps consisting in:

a) mounting the workpiece on the support means so that the or one of the axes of revolution of the workpiece extends substantially vertically;

b) inclining the workpiece by means of the tilting means;

c) causing the workpiece to rotate about the above-specified axis of revolution; and d) spraying the liquid, such as an emulsifier, into the or each inner cavity of the workpiece and sucking up the sprayed liquid from the or each cavity.

The method may include, after step d), a step of spraying water into the at least one inner cavity of the workpiece and of sucking up the sprayed water from the or each cavity.

By way of example, the workpiece is a turbine engine drum. The workpiece may be set into rotation automatically or by an operator using means that may be manual or motor-driven.

The duration for spraying the liquid and/or water is preferably predetermined. Under such circumstances, the time required for processing the part is well controlled.

BRIEF DESCRIPTION OF THE SEVERAL VIEWS OF THE DRAWINGS

The invention can be better understood and other characteristics, details, and advantages appear more clearly on reading the following description made by way of non-limiting example and with reference to the accompanying drawings, in which:

FIG. 6 is a diagrammatic perspective view of the frame of support means of the device shown in FIGS. 2 and 3;

FIG. 7 is a diagrammatic perspective view of the tray of the support means of the device shown in FIGS. 2 and 3;

FIG. 8 is a diagrammatic perspective view of the lever of tilting means of the device shown in FIGS. 2 and 3;

FIG. 9 is a diagrammatic perspective view of a spray manifold of the device shown in FIGS. 2 and 3;

FIG. 10 is a diagrammatic plan view of the FIG. 9 spray manifold;

FIG. 11 is a diagrammatic perspective view of the recovery manifold of the device shown in FIGS. 2 and 3; and FIG. 12 is a highly diagrammatic view of the fluid circuits of the device shown in FIGS. 2 and 3.

DETAILED DESCRIPTION OF THE INVENTION

Figure 1:
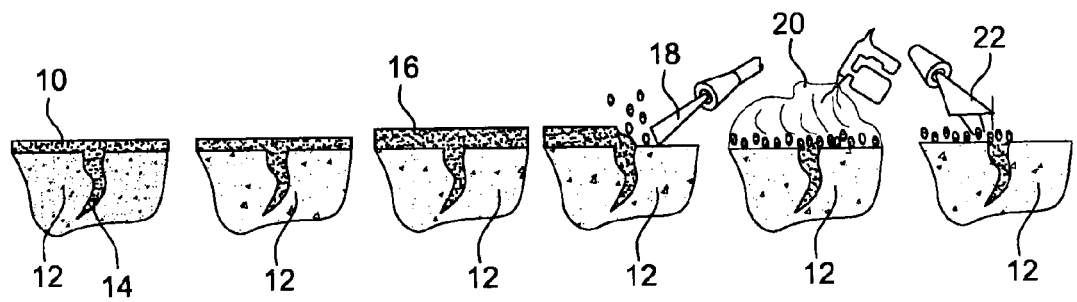
FIG. 1 is a highly diagrammatic fragmentary view in section of a workpiece being inspection by a dye penetration method, and it shows the workpiece during a plurality of successive steps in the method.

Reference is made initially to FIG. 1, which is a diagram showing steps in a dye penetration method applied to a workpiece in order to inspect its surface state.

The workpiece, e.g. a turbine engine part, may include surface defects such as cracks that are visible under ultra-violet light after dye penetration.

The dye penetration method comprises a first step in which a dye known as a "penetrant" 10 is applied to the surface of the workpiece 12 for inspection. The penetrant 10 has high wetting power and it penetrates into the surface defects of the workpiece 12, such as a crack 14 as shown in the first diagram on the left of FIG. 1. The surface of the part is then subjected to pre-washing in order to remove surplus penetrant (second diagram in FIG. 1).

An emulsifier 16 is then applied to the surface of the workpiece 12 which is then washed in water 18, this stage serving to clean the surface of the workpiece and to remove any penetrant that has remained on the surface (third and fourth diagrams in FIG. 1). After this stage, only defects in the surface of the workpiece contain penetrant. In the prior art, the operations of washing the workpiece with an emulsifier and water are performed by immersing the workpiece in vessels filled with those liquids.

The washing stage is followed by stoving the workpiece in order to eliminate water by evaporation.

A developer 20 is then applied to the surface of the workpiece so as to make the penetrant visible under ultra-violet light 22 (fifth and sixth diagrams in FIG. 1).

The device of the invention as described below is adapted particularly, but not exclusively, to performing the above-mentioned stage of washing a workpiece with an emulsifier and water in a controlled length of time.

Figure 2:
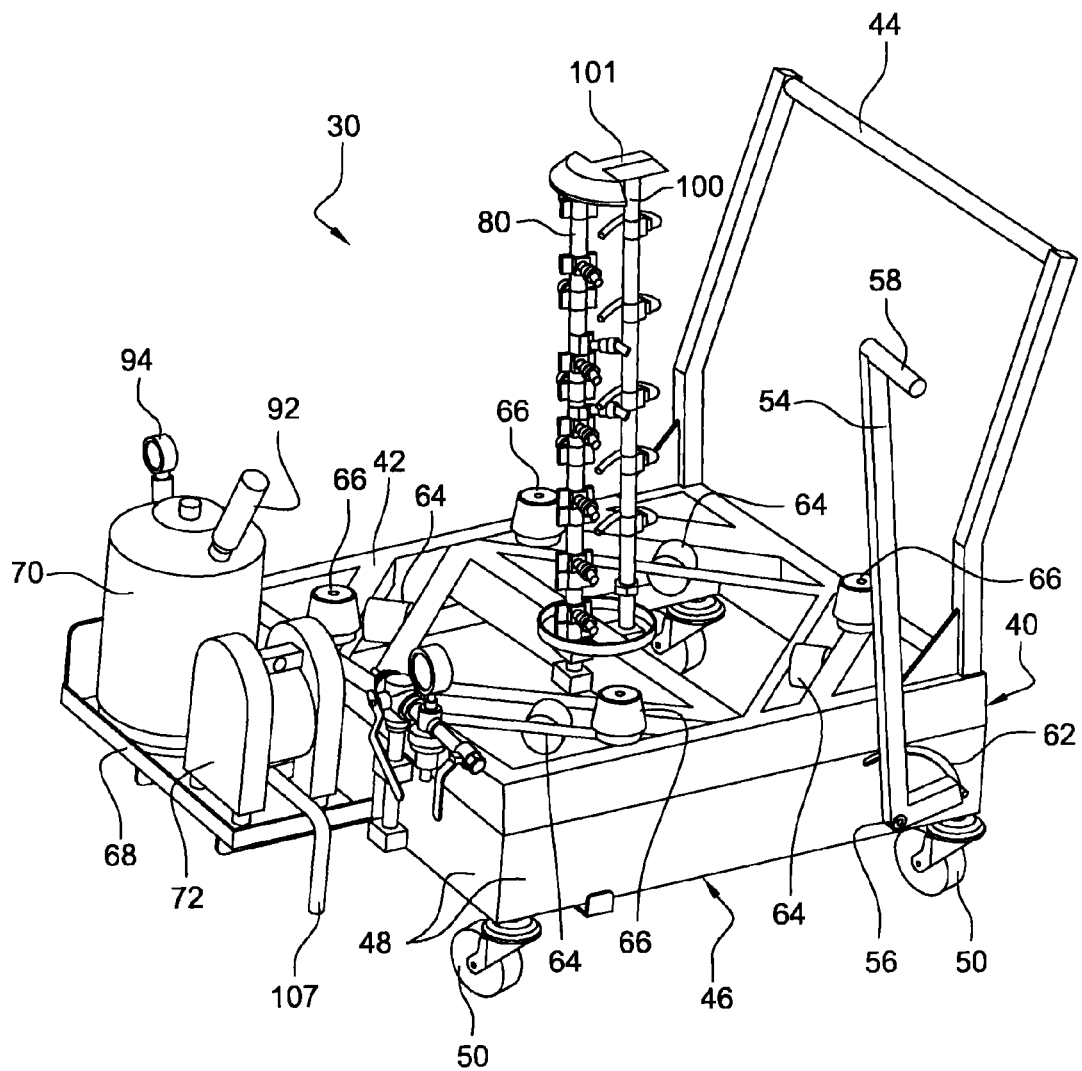
FIGS. 2 and 3 are diagrammatic perspective views of a device of the invention for spraying at least one inspection liquid into at least one internal cavity of a workpiece.
Figure 3:
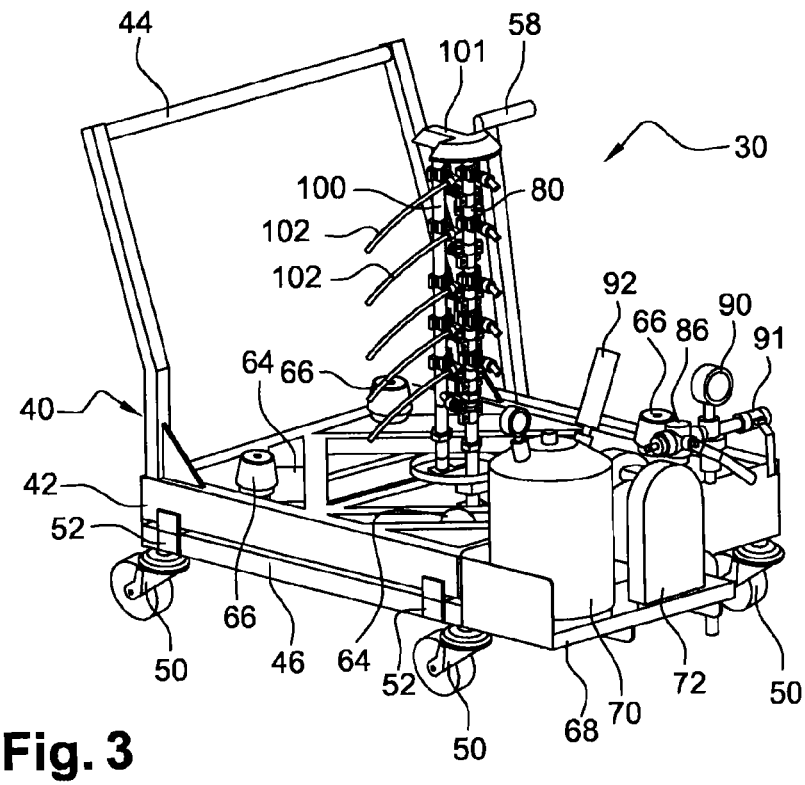
Figure 4:
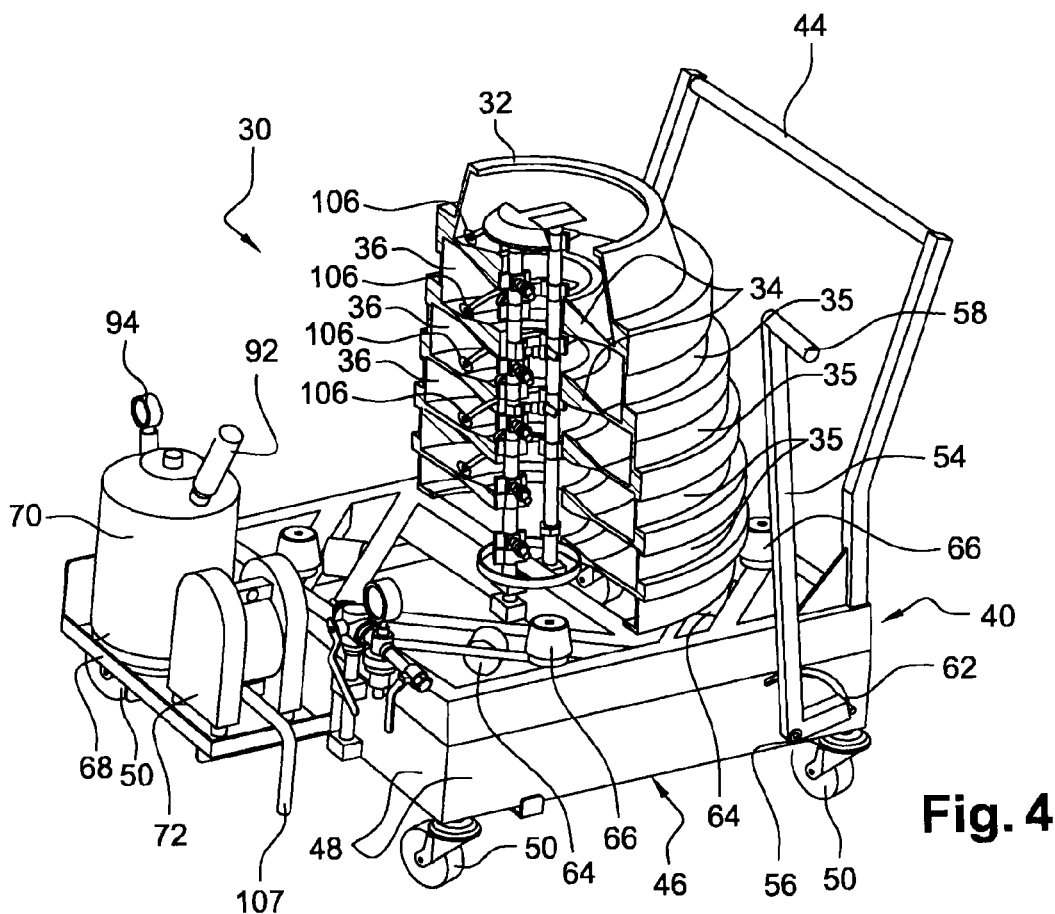
FIGS. 4 and 5 are diagrammatic perspective views of the device of FIGS. 2 and 3 having mounted thereon a workpiece for inspecting by dye penetration, the workpiece being a drum of a turbine engine that is shown in axial section and in perspective.
Figure 5:
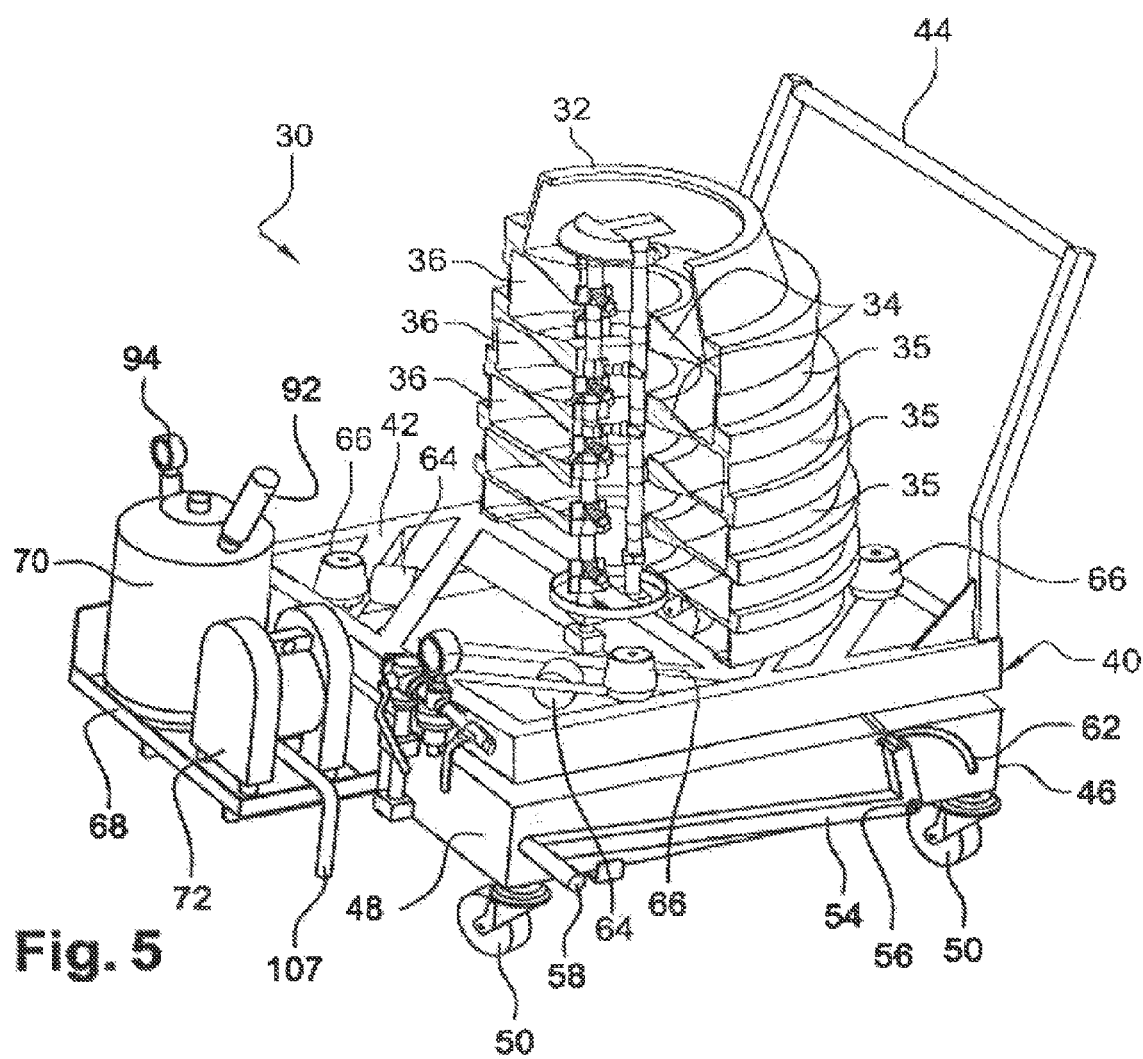

FIGS. 2 and 3 show an embodiment of the device 30 of the invention, with a workpiece for inspection being mounted on that device as shown in FIGS. 4 and 5, the workpiece in this example being a turbine engine drum 32.

The drum 32 comprises a plurality of rotor disks 34 in axial alignment that are connected to one another by cylindrical walls 35 and that define between them internal annular cavities 36 having walls (i.e. the side surfaces of the disks 34 and the radially inner surfaces of the cylindrical wall 35) that need to be inspected in order to verify their surface state. In this example, the device 30 is for spraying the emulsifier and water into each inner cavity 36 of the drum.

The device 30 of the invention comprises the following elements:
- support means 40 for supporting the drum 32 and tilting means for tilting at least a portion of the support means 40 so as to be able to incline the drum 32;
- delivery and spray means 80 for delivering and spraying the emulsifier and water in succession into the inner cavities 36 of the drum 32; and
- suction and discharge means 100 for sucking up and discharging the emulsifier and the water that has been sprayed into the inner cavities 36.

The support means 40 form a carriage in the example shown. They comprise a tray 42 for supporting the drum 32, which tray is rectangular in shape with one of its sides being connected to a horizontal bar 44 for handling and moving the support means (FIG. 7). The tray 42 is mounted on a frame 46 (FIG. 6) that is likewise of rectangular shape, having a vertical peripheral rim 48 that extends along three sides of the frame and around three corresponding sides of the tray 42 when the tray is resting on the frame, as shown in FIG. 2.

Castors 50 are fastened to the four corners of the frame 46 in order to allow the support means to be moved, these movements being performed by an operator using the above-mentioned horizontal bar 44.

The tray 42 is pivotally mounted on the frame 46 and is movable from a horizontal position in which the tray and the frame are substantially horizontal and parallel (FIGS. 2 to 4), to an inclined position in which the frame remains substantially horizontal while the tray adopts an inclined position, e.g. at an angle of about 10° to 20° relative to the frame (FIG. 5).

In the example shown, the tray 42 is pivotally mounted on the frame 46 by means of hinges 52 connecting one of the sides of the tray to the corresponding side of the frame, which in this example is the side of the frame that does not have a vertical peripheral rim 48 (FIG. 3). The hinges define a pivot axis for the substantially horizontal tray.

The tray 42 is pivoted by an operator using a tilting lever 54, which is shown in FIG. 8.

The lever 54 is generally L-shaped, having two rectilinear portions that are connected together via one end of each portion. The junction zone between these rectangular portions is hinged about a substantially horizontal axis 56 carried by the frame 46 (FIGS. 2, 4, and 5). In the example shown, the frame 46 has an orifice 58 for receiving a shaft on this axis, which is situated at the side of the frame opposite from the side carrying the hinges 52 for pivoting the tray 42.

The lever 54 can be pivoted about the axis 56 between a position shown in FIG. 5, and a position shown in FIGS. 2 and 4.

At its free end (i.e. its end remote from the axis 56), the longer portion of the lever 54 carries a handle 58, and at its free end (i.e. remote from the axis 56), the shorter portion of the lever carries a finger 60. The finger 60 is engaged in and movable along a through slot 62 of curved shape in the vertical rim 48 of the frame. The tray 42 bears against the finger 60, which is moved along the slot 62 in the frame so as to pivot the tray about the axis defined by the hinges 52.

When the lever 54 is in the position shown in FIGS. 2 to 4, where the longer portion of the lever is substantially vertical, the finger 60 is situated at a "low" end of the slot 62 and is interposed between the frame and the tray 42, the tray being substantially horizontal, i.e. being in its non-inclined position. When the lever 54 is in the position shown in FIG. 5, where the longer portion of the lever is substantially horizontal, the finger is situated at a "high" end of the slot 62 and supports the tray in its inclined position.

The movement of the lever about the shaft 56 (through about 90°) thus causes the finger 60 to move along the slot 62 in the frame 46 and leads to the tray 42 pivoting about the axis defined by the hinges 52 (through about 10° to 20°).

The support means 40 also include centering and guide means for centering and guiding the drum 32 in rotation relative to its longitudinal axis or axis of revolution. In the example shown, these means comprise wheels or rollers 64, 66 carried by the tray 42. The tray 42 has first rollers, there being four of them in the example shown, that are regularly distributed around a circumference centered on the axis of revolution of the drum, two of these rollers being mounted to rotate freely about a first substantially horizontal axis and the other two rollers being mounted to rotate freely about another substantially horizontal axis that is perpendicular to the first axis. The drum 32 is designed to stand vertically on the rollers 64, which rotate about their axes when the drum is itself turned relative to the tray.

The tray 42 has second rollers, there being four of them in the example shown, each of which is mounted to rotate freely about a respective substantially vertical axis, which rollers are regularly distributed around a circumference centered on the axis of revolution of the drum. The drum comes to bear laterally against these rollers, which rotate about their respective axes when the drum is turned relative to the tray.

The support means 40 also include a plate 68 for supporting a container 70 of emulsifier and a pump 72, this plate being carried by the frame 46 at its side remote from the side where the tray 42 is connected to the horizontal bar 44. The container 70 contains a volume of emulsifier which, by way of example, may be about 10 liters (L), which is sufficient for processing a turbine engine drum.

The device of the invention has two manifolds 80 and 100 that are used respectively for delivering and spraying the emulsifier and water into the inner cavities of the drum, and for recovering the emulsifier and the water that have been injected into these inner cavities by sucking them up and discharging them.

The delivery manifold 80, shown more clearly in FIG. 9, is substantially rectilinear and has one end fastened to the tray substantially in its middle. The manifold 80 is substantially vertical, it passes through the drum 32 longitudinally, and it is substantially parallel to the longitudinal axis of the drum.

The manifold 80 carries a plurality of spray nozzles 82. In the example shown, the manifold 80 carries three series of nozzles 82, each series having five or six nozzles. The nozzles 82 in each series are spaced apart and in alignment relative to one another in a plane that is substantially vertical, with each of these planes being angularly offset from the planes of the other series of nozzles. As can be seen diagrammatically in FIG. 10, two series of nozzles 82 extend in diametrically opposite planes about the axis of the manifold 80, while the third series of nozzles is situated in a plane that is offset by about 45° from one of those planes.

As can be seen in FIG. 9, some of the nozzles 82 have their outlet orifices pointing downwards and others have them pointing upwards so that the liquids are sprayed over the entire surfaces of the inner cavities of the drum. In this example, the drum 32 has six inner cavities 36, with each inner cavity receiving the liquids sprayed by two or three nozzles 82. The outlet pressure of the liquid leaving the nozzles may for example be about two bars.

As shown diagrammatically in FIG. 12, the bottom end of the delivery manifold 80 is connected by a duct 84 to the outlet of a three-port valve 86 having a first inlet connected to the above-mentioned emulsifier container 70 and having a second inlet connected to a water tank 88. The duct connecting the three-port valve to the water network may have a pressure gauge 90 and a stop cock 91. The emulsifier container 70 has stirrer means 92 for stirring its content, and possibly also a pressure gauge 94.

The recovery manifold 100, shown more clearly in FIG. 11, is substantially rectilinear and vertical, its bottom end being fastened to the tray 42 substantially at its middle. The manifold 100 passes longitudinally through the drum 32 and it is substantially parallel to and a short distance from the other manifold 80.

The manifold 100 carries a plurality of suction tubes 102, there being five of them in the example shown. These tubes 102 are regularly spaced apart from one another. They are made of flexible plastics material and each has one end connected to the manifold 100 and an opposite end that is free and designed to be received in the bottom of a cavity 36 in the drum 32 in order to suck up the liquids injected into the cavity.

In the example shown, the drum 32 is inclined so that the lowest zone of each inner cavity of the drum is situated on a side face of one of the disks defining the cavity. The free ends of the suction tubes 102 are situated in these zones 106, which are represented diagrammatically by circles in FIG. 4.

While the drum 32 is being processed, the emulsifier or water that is sprayed into the cavities flows under gravity along the inside surfaces of the cavities 36 to the above-mentioned zones from which it is sucked out by the tubes.

As shown diagrammatically in FIG. 12, the bottom end of the recovery manifold 100 is connected by a duct to the above-mentioned pump 72 having an outlet 107 for discharge purposes. The container 70 is connected to an air feed network 108 by a duct 109 having a pressure gauge 110 and a stop cock 111. The pump 72 is connected to this duct 109 via another duct 112 having a flow rate regulator 113 and an isolating valve 114. The references 116 in FIG. 12 designate quick couplings.

The top ends of the manifolds 80 and 100 are fastened to an element 101 for centering and guiding the drum 32 when it is mounted on the device. In the example shown, this element 101 has peripheral edge portions of convex curved shapes that are substantially complementary to the inner peripheral edges of the disks 34 of the drum. While the drum is being put into place on the device, the drum is positioned above the manifolds 80 and 100 and is moved vertically downwards so that the manifolds pass longitudinally through the drum. During this passage, the element 101 co-operates with the inner peripheral edges of the disks 34 in order to guide and center the drum 32. Once the drum is in place, the element 101 may be covered by a cover (not shown) for the purpose of closing the top inner cavity 36 of the drum and thus preventing emulsifier and water being projected out from the drum while it is being processed.

The device 30 of the invention may be used as follows.

The tray 42 is arranged horizontally, i.e. the lever 54 is in the position shown in FIGS. 2 to 4. The drum 32 is put into place on the tray 42. As described above, the drum 32 is positioned over the device and is then moved downwards until the manifolds 80 and 100 pass longitudinally through the drum and the drum is standing on the rollers 64 of the tray. The lever 54 is then moved from its position shown in FIGS. 2 to 4 to its position shown in FIG. 5 so that the tray 42 is inclined. In this position, the drum 32 is inclined and the manifolds that extend parallel to the axis of the drum and that are secured to the tray are likewise inclined. Emulsifier is sprayed into the inner cavities of the drum 32 via the delivery manifold 80 and the spray nozzles 82, the emulsifier flowing under gravity along the inside surfaces of the cavities to the zones 106 from which it is sucked up and recovered by the manifold 100. During this operation, an operator causes the drum 32 to be set into rotation using manual or motor-driven means so that the emulsifier can be sprayed onto the entire surface of each inner cavity. This operation lasts for about 1 minute. By way of example, the emulsifier used is a product with the reference ER83 A as sold by the supplier Sherwin and it is diluted to 5% in water. Thereafter, it suffices to operate the valve 86 so as to feed the manifold 80 with water, which can be done quickly.

Water is then sprayed into the inner cavities of the drum via the delivery ramp 80 and the spray nozzles 82. This water flows under gravity to the zones 106 from which it is sucked up and recovered by the manifold 100. During this operation, an operator likewise causes the drum 32 to be set into rotation by manual or motor-driven means so that the entire surface of each inner cavity can be rinsed with water. This operation lasts for about 1 minute, so the total time required for spraying the drum is about 2 minutes, in this particular embodiment of the invention.

In a variant that is not shown, the manifolds could be movable relative to the tray in order to optimize their positions relative to the workpiece for processing, in order to be able to process workpieces of different sizes. This movement may be performed manually or with the help of a motor.

In yet another variant that is not shown, the device could include another delivery manifold that is fitted with spray nozzles and that extends on the outside of the workpiece in order to spray liquid onto the outer surface of the workpiece simultaneously with processing its inner cavities.

The invention claimed is:

1. A device for spraying at least one liquid for use in dye penetration inspection into an inner cavity of a workpiece, the device comprising:
   a support which supports the workpiece;
   a liquid delivery manifold that is connected to a tank and to a spray nozzle which sprays the liquid, at least part of the liquid delivery manifold being for receiving inside the workpiece when the workpiece is in position mounted on the support to enable the liquid to be sprayed into the inner cavity of the workpiece;
   a recovery manifold for recovering the sprayed liquid, which recovery manifold is for receiving at least in part inside the workpiece when the workpiece is in position mounted on the support, and is connected to a suction tube which extends into the inner cavity of the workpiece and sucks up the liquid sprayed into the inner cavity of the workpiece, and to a pump which discharges the sucked-up liquid; and
   a tilting lever which tilts at least a portion of the support from a horizontal position to an inclined position in which the workpiece is to be inclined so that the sprayed liquid in the inner cavity of the workpiece flows under gravity to at least one zone from which the sprayed liquid is sucked up by the suction tube, wherein said liquid delivery manifold and said recovery manifold are secured to said at least a portion of the support.

2. A device according to claim 1, wherein the support comprises centering and guide rollers which guide the workpiece in rotation about an axis, or an axis of revolution of the workpiece.

3. A device according to claim 2, wherein the centering and guide rollers comprise a first series of rollers, each roller of the first series of rollers free to rotate about an axis that is perpendicular to the axis of rotation of the workpiece, and a second series of rollers, each roller of the second series of rollers free to rotate about an axis parallel to the axis of rotation of the workpiece.

4. A device according to claim 1, wherein the support comprises a tray of rectangular shape that is mounted on a frame and that is connected to the frame by hinges enabling the tray to be pivoted relative to the frame about a horizontal axis extending parallel to one of sides of the tray.

5. A device according to claim 4, wherein the frame has a vertical peripheral rim extending around at least a fraction of the tray.

6. A device according to claim 5, wherein the tilting lever comprises an L-shaped lever comprising a first rectilinear portion connected to a second rectilinear portion, the first rectilinear portion carrying a handle, a junction zone between the first and second rectilinear portions being hinged to the frame about a horizontal axis, and the second rectilinear portion carrying a finger that is engaged in and movable along a slot of curved shape in the peripheral rim of the frame and that co-operates with the tray to cause the tray to pivot when the finger moves along the slot.

7. A device according to claim 1, wherein the support is fitted with castors to enable the device to be moved.

8. A device according to claim 1, wherein the support includes a support plate for supporting the tank, the tank is connected to the pump connected to the recovery manifold.

9. A device according to claim 8, wherein the delivery manifold is connected by a three-port valve to the tank for liquid and to a water supply network.

10. A device according to claim 1, wherein the recovery manifold is rectilinear and carries a plurality of suction tubes that are flexible and spaced apart from one another, each of the suction tubes having a free end that is to be received in inner cavities of the workpiece.

11. A device according to claim 1, wherein the delivery manifold is rectilinear and carries at least two series of spray nozzles, the spray nozzles in each series being spaced apart from one another and being situated in a plane that is vertical and that is angularly offset from the plane of the other series of spray nozzles.

12. A method of spraying at least one liquid for use in dye penetration inspection into an inner cavity of a workpiece by the device of claim 1, the method comprising:
 a) mounting the workpiece on the support so that an axis of revolution of the workpiece extends vertically;
 b) inclining the workpiece by the tilting lever;
 c) causing the workpiece to rotate about the axis of revolution; and
 d) spraying the liquid, or an emulsifier, into the inner cavity of the workpiece and sucking up the sprayed liquid from the cavity.

13. A method according to claim 12, further comprising, after d), e) spraying water into the inner cavity of the workpiece and sucking up the sprayed water from the inner cavity of the workpiece.

14. A method according to claim 12, wherein the workpiece is a turbine engine drum.

15. A method according to claim 12, wherein the workpiece is set into rotation automatically or manually or motor-driven by an operator.

16. A method according to claim 12, wherein a duration for spraying the liquid is predetermined.

* * * * *